United States Patent [19]

Tassano

[11] 4,112,744

[45] Sep. 12, 1978

[54] APPARATUS FOR DETECTING WATER IN OIL

[75] Inventor: Peter Francis Tassano, Reading, England

[73] Assignee: Lucas Industries Limited, Birmingham, England

[21] Appl. No.: 777,537

[22] Filed: Mar. 14, 1977

[30] Foreign Application Priority Data

Mar. 13, 1976 [GB] United Kingdom ............... 10158/76

[51] Int. Cl.² .......................................... G01N 27/22
[52] U.S. Cl. .............................. 73/61.1 R; 324/61 R
[58] Field of Search ............................ 73/61.1 R, 73; 324/61 R, 61 QS

[56] References Cited

U.S. PATENT DOCUMENTS

| 2,934,700 | 4/1960 | Holaday et al. .................. 324/61 R |
| 3,215,931 | 11/1965 | Schooley, Jr. ..................... 324/61 R |
| 3,546,926 | 12/1970 | Dunavent, Jr. et al. ......... 73/61.1 R |

*Primary Examiner*—Charles A. Ruehl

[57] ABSTRACT

In an apparatus for detecting water in oil a capacitive probe is filled with the oil under test. This probe and a reference capacitor are alternately connected in the frequency determining network of an h.f. oscillator, the output of which is connected to a frequency to voltage converter. A sample and hold circuit gated in synchronism with switching of the capacitors and an amplifier a.c. coupled to the sample and hold circuit provides an a.c. output, a change in the amplitude of which indicates changes in the dielectric constant of the oil.

13 Claims, 7 Drawing Figures

APPARATUS FOR DETECTING WATER IN OIL

This invention relates to apparatus for the detection of water in oil and has as an object to provide such apparatus in a convenient form.

Apparatus in accordance with the invention comprises a capacitive probe unit through which the oil under test is caused to flow, a reference capacitor, switch means alternately connecting the capacitive probe and the reference capacitor into the circuit of an oscillator whereby the oscillator frequency is determined in alternate periods by the dielectric constant of the oil, a frequency to d.c. voltage converter connected to the output of the oscillator, filter means connected to the output of the converter for producing a signal fluctuating at the frequency of operation of said switch means and indicator means a.c. coupled to the output of the filter means sensitive to the amplitude of said fluctuating signal.

Preferably the filter means includes a sample and hold circuit operated in synchronism with said switch means.

The indicator means may include an active full-wave rectifier circuit either with a current measuring meter in its feedback loop or driving a voltmeter. In addition the indicator means may include a trigger circuit set to operate at a predetermined signal level and arranged to operate one or more warning device and/or a relay which may be part of a control system controlling oil flow through the probe.

An example of the invention is shown in the accompanying drawings in which.

The apparatus shown in FIGS. 1 to 4 includes a capacitive probe device 10 which is mounted in an oil pipe line so that the oil flowing along the line passes through the probe which is preferably arranged with its outlet lowermost to avoid separated water collecting therein. An electronic switching device 11 in the form of an integrated circuit switch type DG 133 BP is used to connect the probe 10 and a reference capacitor 13 to an h.f. oscillator 14 operating at a frequency in the region of 50 KHz, but dependent on the value of the capacitor to which it is connected by the device 11.

Figure 2:
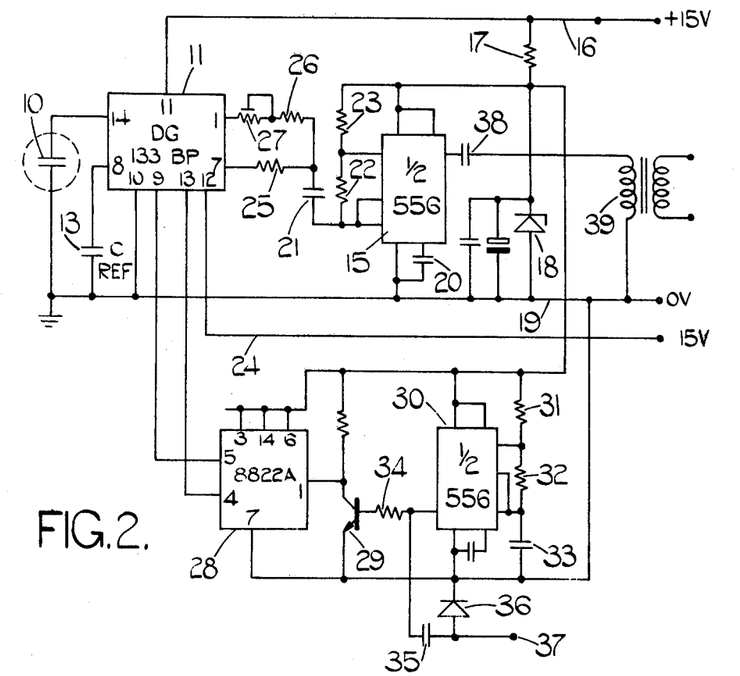
FIG. 2 is a circuit diagram of a part of the circuit of FIG. 1 including a probe, a reference capacitor, an h.f. oscillator and a switch arrangement for alternately connecting the probe and the reference capacitor in the oscillator circuit.

As shown in detail in FIG. 2 the oscillator 14 includes an integrated circuit timer 15 type 555 (or half of a duel timer type 556) connected as an astable multi-vibrator. The timer 15 is supplied with a low voltage regulated voltage supply from a +15V supply rail 16 via a resistor 17 with a zener diode 18 connected between the resistor/timer connection and an earth rail 19. The RESET and Vcc terminals of the timer 15 are connected to the cathode of the zener diode 18 and its GROUND terminal is connected to rail 19. The CONTROL VOLTAGE terminal of the timer is connected to the rail 19 by a capacitor 20. The TRIGGER and THRESHOLD terminals of the timer are connected together and to one side of a capacitor 21 and also by a resistor 22 to the DISCHARGE terminal of the timer. This DISCHARGE terminal is also connected via a resistor 23 to the cathode of the zener diode 18.

The device 11 is a two channel J-FET switch device. One channel provides a low resistance path between pins 1 and 14 of the device when the signal on pin 13 is high and a high resistance path when the signal on pin 13 is low. In the other channel there is a low resistance path between pins 7 and 8 when the signal on pin 9 is high and a high resistance path when the signal on pin 9 is low. Pins 11 and 12 are connected to the rail 16 and a −15V rail 24 respectively and pin 10 is grounded to rail 19. Pin 7 is connected to the other side of the capacitor 21 by a resistor 25 and pin 1 is connected to said other side of the capacitor 21 by a resistor 26 and a variable resistor 27 in series. Pin 14 is connected to one side of the probe 10, the other side of which is earthed and pin 8 is connected by the reference capacitor 13 to the earth rail 19. The timer 15 operates in known manner to produce at its OUTPUT terminal an oscillating signal of frequency determined by the values of the components 21, 22, 23 and 25 and 13 or 26, 27 and 10 depending on which channel of the device 11 is at low resistance. The variable resistor 27 can be adjusted as will be further explained hereinafter.

Pins 9 and 13 of the device 11 are connected to the output terminals of a flip-flop circuit 28 type 8822A which is driven through a direct-coupled inverting transistor amplifier 29 from an oscillator constituted by another 555 type timer 30 (which may be the other half of a 556 timer used for timer 15). This is again connected as an astable multivibrator using resistors 31 and 32 and a capacitor 33 as timing components. The OUTPUT terminal of the timer 30 is connected to the base of transistor 29 by a resistor 34 and also by a capacitor 35 to the anode of a diode 36, which has its cathode grounded to the rail 19. A terminal 37 for the control of a sample and hold circuit to be described hereinafter is connected to the anode of the diode 36.

The OUTPUT terminal of the timer 15 is connected by a capacitor 38 to one end of the primary winding of a transformer 39 the other end of which is grounded to rail 19. The secondary winding of the transformer 39 is connected to a frequency to voltage converter 40 which is shown in detail in FIG. 3. This converter includes a pair of complementary transistors 41, 42 with their emitters interconnected and connected to one end of the secondary winding of the transformer 39 and their bases interconnected and connected to the other end of the secondary winding. The collector of the n-p-n transistor 41 is connected by a resistor 43 to the rail 16 and the collector of the p-n-p transistor 42 is connected by two resistors 44, 45 in series to the rail 19. A capacitor 46 is connected between said one end of the secondary winding and the common point of the resistors 44, 45. A capacitor 47 is connected between the collector of the transistor 41 and the rail 19. The secondary winding of the transformer 39 produces alternate positive and negative going pulses. The positive going pulses turn on the transistor 41 and the negative going pulses turn on the transistor 42. The capacitor 46 is a differentiating capacitor and charges while the transistor 41 is conducting via resistors 43 and 45 and discharges when transistor 42 is conducting via the resistor 44. Thus two pulses are produced in each cycle of the oscillator 14.

Figure 3:
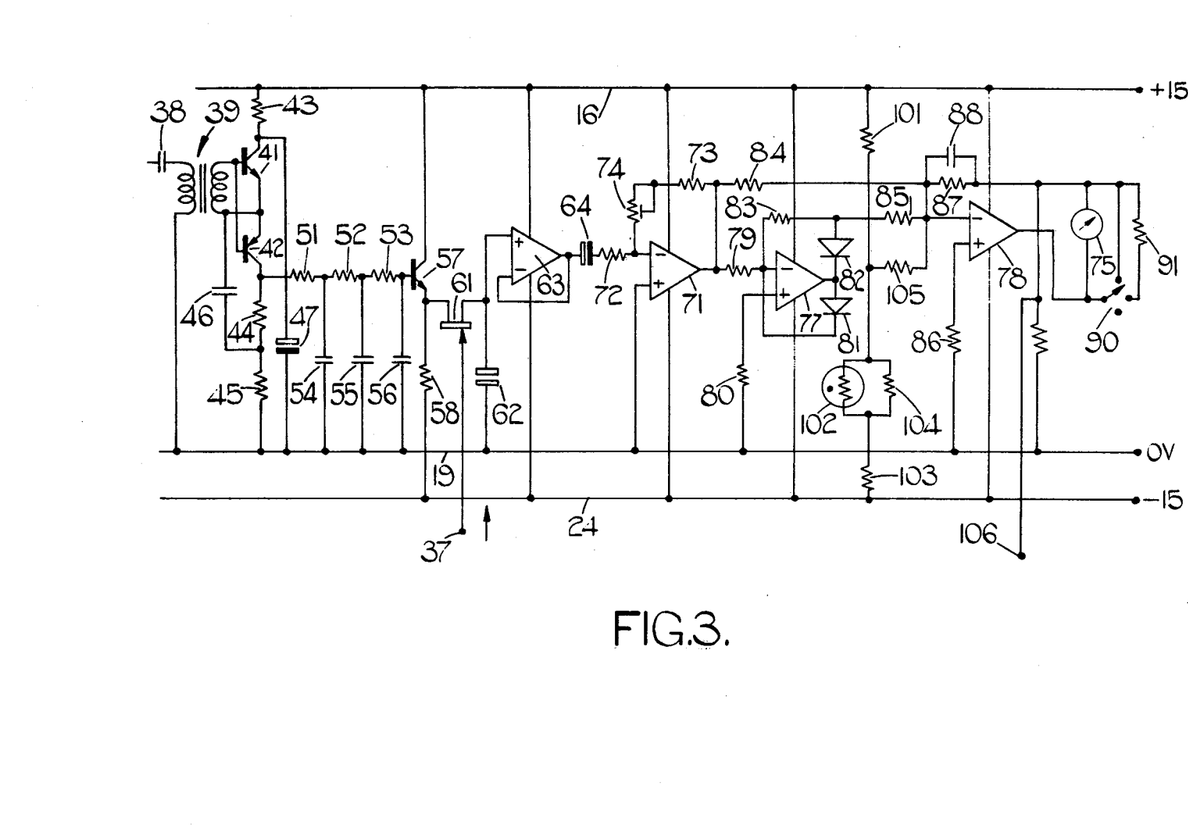
FIG. 3 is a circuit diagram of another part of the circuit including a frequency to voltage converter, a filter circuit, an a.c. amplifier and an active full-wave rectifier circuit.

The frequency to voltage converter also includes a passive filter circuit fed from the collector of the transistor 42. This filter includes three resistors 51, 52, 53 connected in series and three capacitors 54, 55, 56 connecting the ends of the resistors to the rail 19 in the usual R-C filter configuration. The passive filter circuit converts the pulses at the collector of the transistor 42 into a d.c. voltage dependent on the frequency of these pulses. A transistor 57 has its base connected to the resistor 53, its collector connected to the rail 16 and its emitter connected by a resistor 58 to the rail 24. The transistor 57 buffers the passive filter circuit, and feeds a sample and hold circuit 60.

The sample and hold circuit 60 comprises an f.e.t. 61 with its drain-source path connecting the emitter of the transistor 57 to one side of a capacitor 62, the other side of which is grounded to the rail 19. A differential amplifier 63 connected as a high input impedance unity gain buffer has its non-inverting input terminal connected to said one plate of the capacitor 62. The gate of the f.e.t. 61 is connected to terminal 37. The control pulses at the terminal 37 are synchronous with those applied to the flip-flop 28 but are inverted due to the action of the transistor 29. The f.e.t. conducts, therefore, for a short time in each cycle immediately before the switching operation starts and well after the spikes resulting from the previous switching operation have disappeared.

The output of the buffer 63 is a.c. coupled by a capacitor 64 to an amplifier 70. This amplifier 70 is in the form of an operational amplifier 71 with an input resistor 72 connected to its inverting input terminal and a resistor 73 and a variable resistor 74 in series providing feedback from its output terminal to its inverting input terminal. The non-inverting input terminal of the amplifier 71 is grounded to the rail 19.

The amplifier 70 drives a meter 75 via an active full-wave rectifier circuit 76 of known form utilizing two operational amplifiers 77 and 78. The amplifier 77 is connected as a fast half-wave rectifier with its inverting input terminal connected to the output terminal of the amplifier 71 by a resistor 79 and its non-inverting input terminal connected to the rail 19 by a resistor 80. Feedback is provided by a diode 81 with its anode connected to the output terminal of the amplifier 77 and its cathode connected to the inverting input terminal and by a further diode 82 with its cathode connected to the output terminal of the amplifier 77 and its anode connected by a resistor 83 to the inverting input terminal of the amplifier 77. The resistors 79 and 83 are both of the same ohmic value so that for positive half cycles of the input the amplifier acts as a unity gain inverting amplifier, but for negative half cycles feedback is via the diode 81, so that the output, which is taken from the anode of the diode 82 is very close to the signal earth voltage at the non-inverting input terminal of the amplifier 77.

The amplifier 78 has an input to its inverting input terminal from the output of the amplifier 71 via a resistor 84 and another from the anode of diode 82 via a resistor 85 of half the ohmic value of that of resistor 84. The non-inverting input terminal of the amplifier 78 is connected by a resistor 86 to the rail 19 and feedback is provided through the meter 75 and a resistor 87 in series to the non-inverting input terminal of the amplifier 78. A capacitor 88 is connected across the resistor 87.

The amplifier 78 sums the input signal with twice the inverted half-wave rectified signal from the amplifier 77 so that the final output therefrom is full-wave rectified. The capacitor 88 provides damping of the meter 75, the internal resistance of which (being in the feedback loop of the active full-wave rectifier circuit) does not need to be taken into account.

A switch 90 is provided for switching the meter 75 between various ranges. In one position of switch 90 the meter 75 is bridged by a resistor 91 to shunt some current past the meter. In another position the meter is short circuited and in a final position the switch is open so that all the feedback current flows through the meter.

The switch 90 is used during setting up of the apparatus to avoid damage to the meter.

The full-wave rectifier circuit 76 is provided with a temperature compensation circuit 100 for overcoming the effects of changes in the dielectric constant of the oil undee test with temperature. The circuit 100 includes a resistor 101, a thermistor 102 and a resistor 103 connected in series between the rails 16, 24, a resistor 104 bridging the thermistor 102 and a resistor 105 connecting the junction of the resistor 101 and the thermistor 102 to the summing point of the amplifier 78.

The temperature compensation circuit 100 acts as a variable potential divider, its output, taken from the junction of the resistors 101, 104, 105 and the thermistor 102, being fed via the resistor 105 to the summing point of the amplifier 78. The output voltage of the circuit 100 will thus be inverted by the action of the amplifier 78 to produce an offset voltage. To obtain a meter zero, therefore the variable resistor 27 is adjusted during setting up to vary one of the two frequencies so that in this condition the offset is cancelled out. The variable resistor 27 also allows for a range of the dielectric constant of the oil under test, as occurs for example, when different batches or types of oil are used.

An additional output is taken from the full-wave rectifier circuit at the junction of the meter 75 and the resistor 87. This junction is connected via a terminal 106 to the circuit shown in FIG. 4. This circuit includes an operational amplifier 107 connected as a d.c. voltage comparator with the terminal 106 connected via a resistor 108 to the non-inverting input terminal of the amplifier 107. The inverting input terminal of the amplifier 107 is connected by a resistor 109 to the variable point of a potentiometer 110 one end of which is grounded to the rail 19 and the other end of which is connected via a switch 111 to either of two resistor chains 112, 113. The output terminal of the comparator is connected by resistors 114 and 115 in series to the rail 19 and the common point of these resistors is connected to the gate of an SCR 116, the cathode of which is connected by a normally closed reset switch 117 to the rail 19. The anode of the SCR is connected to the cathode of a diode 118 the anode of which is connected by a resistor 119 to the rail 16. A d.c. energised audible alarm device 120 is connected between the rail 16 and the cathode of the diode 118, so that the alarm sounds whenever the trigger circuit constituted by the SCR 116 is fired. Opening of switch 117 (after the comparator 107 has reset) resets the trigger circuit.

Figure 4:
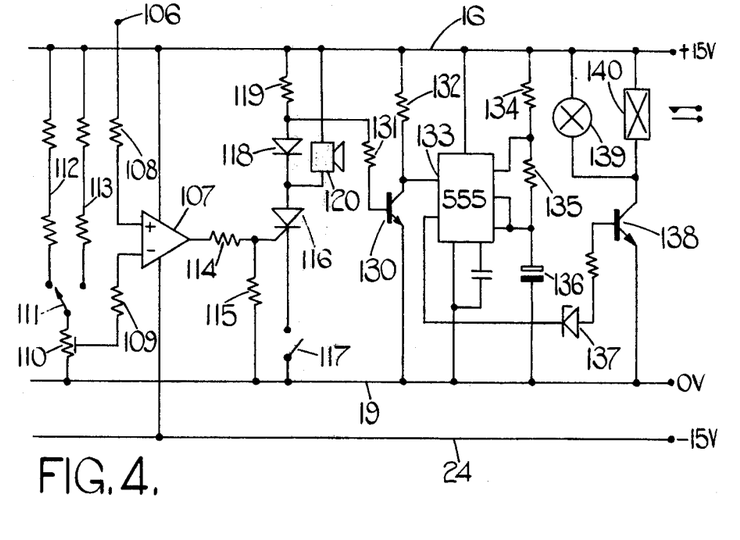
FIG. 4 is a circuit diagram showing a further part of the circuit including a comparator circuit, a trigger circuit and a low frequency oscillator.

A transistor 130 with its emitter grounded to the rail 19 has its base connected by a resistor 131 to the anode of the diode 118. A resistor 132 is connected between the collector of the transistor 130 and the rail 16 so that the transistor 130 acts as a d.c. amplifier controlling the RESET terminal of another oscillator based on a 555 type timer i.c. 133 connected as before as an astable multivibrator using two resistors 134 and 135 and a capacitor 136 chosen to provide a frequency of about 1Hz. The output of the oscillator is connected via a zener diode 137 to drive a transistor 138 controlling a flasher lamp 139 and a relay 140 providing a remote control signal to close down the plant which is to be fed with the oil under test if required.

Figure 1:
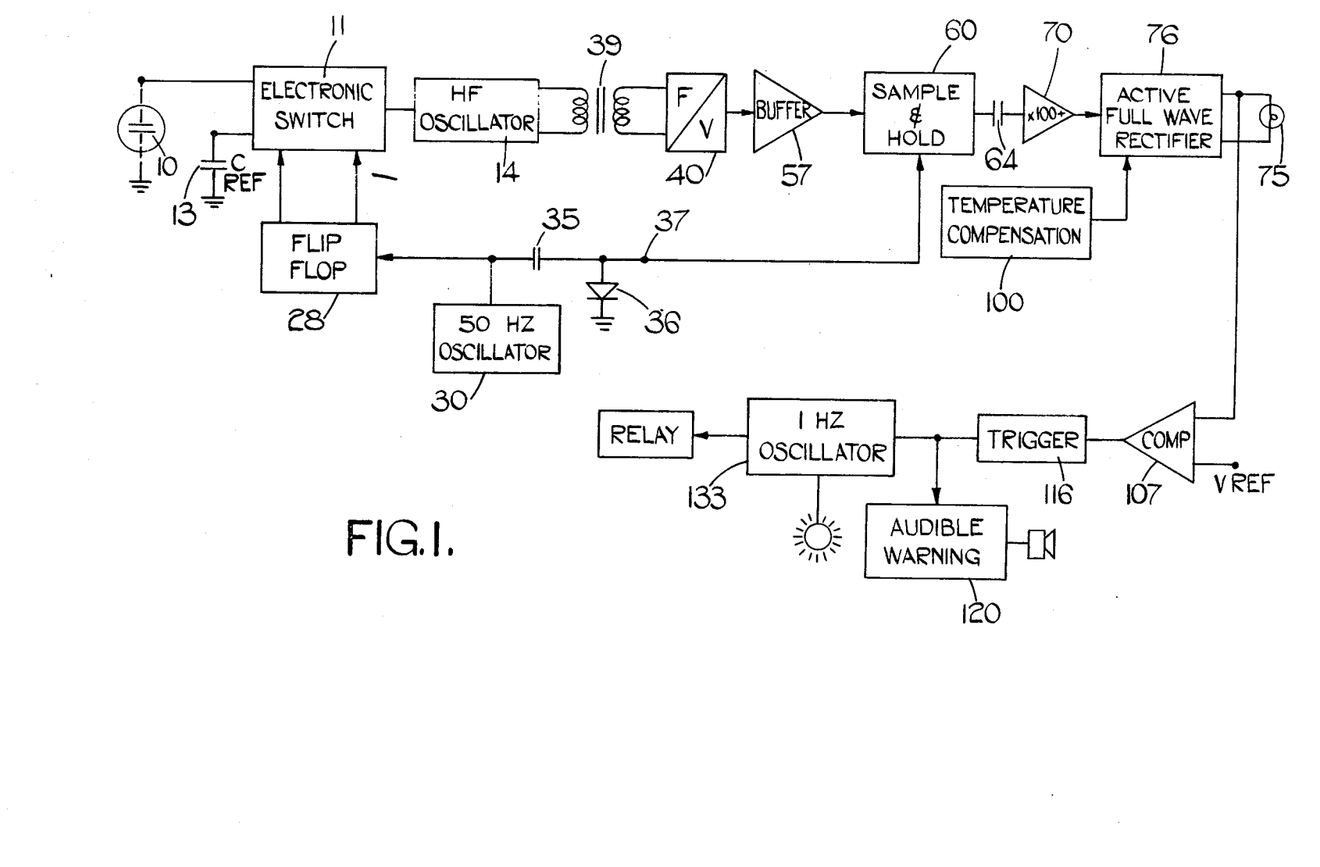
FIG. 1 is a schematic diagram of the apparatus.
Figure 5:
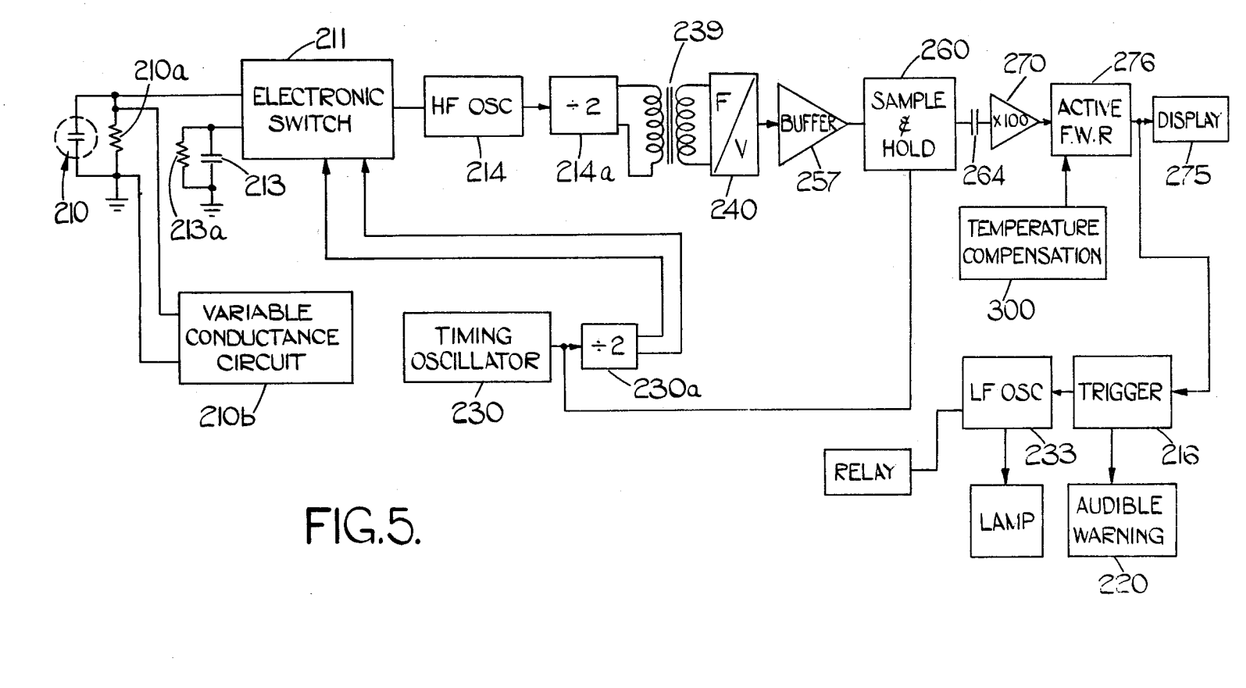
FIG. 5 is a schematic block diagram of another example of the invention and FIGS. 6 and 7 together constitute the full electrical circuit diagram of the example diagrammatically shown in FIG. 5.
Figure 6:
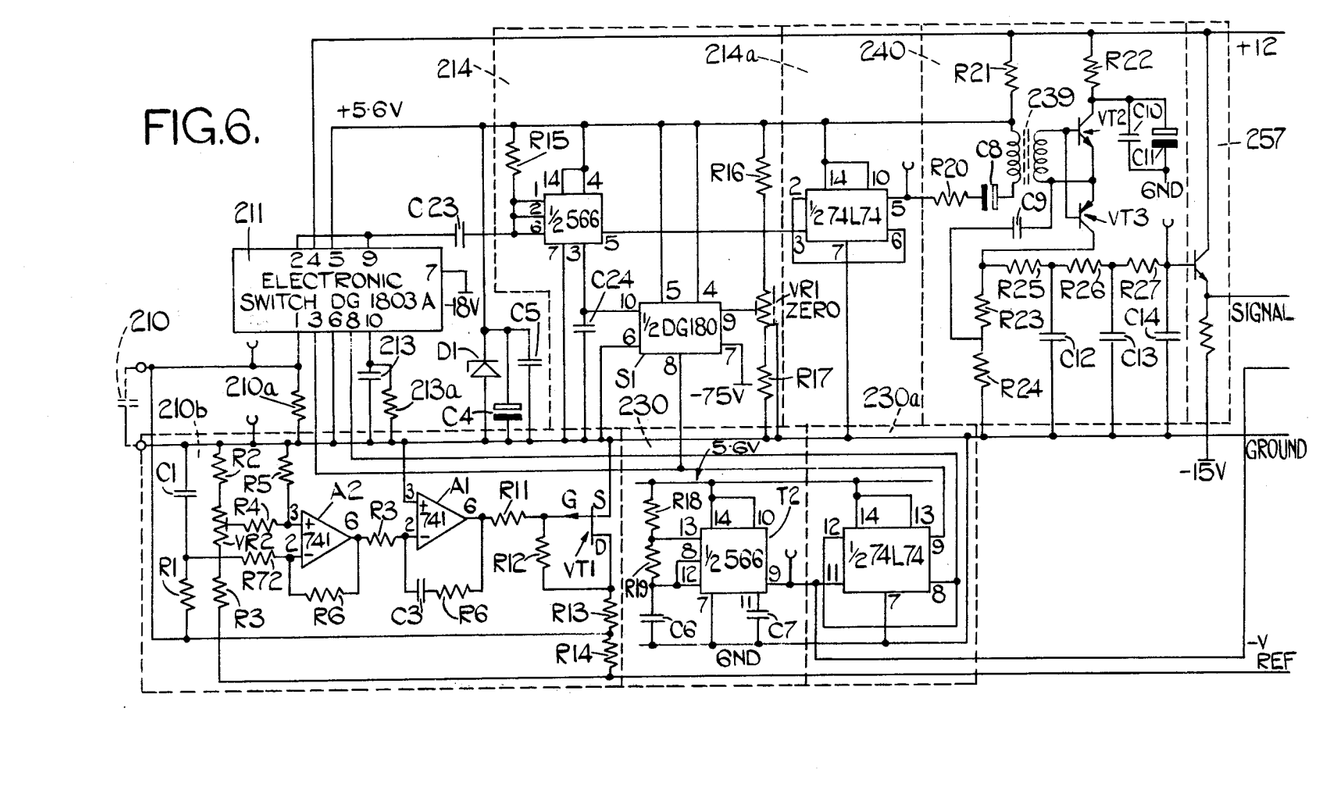
Figure 7:
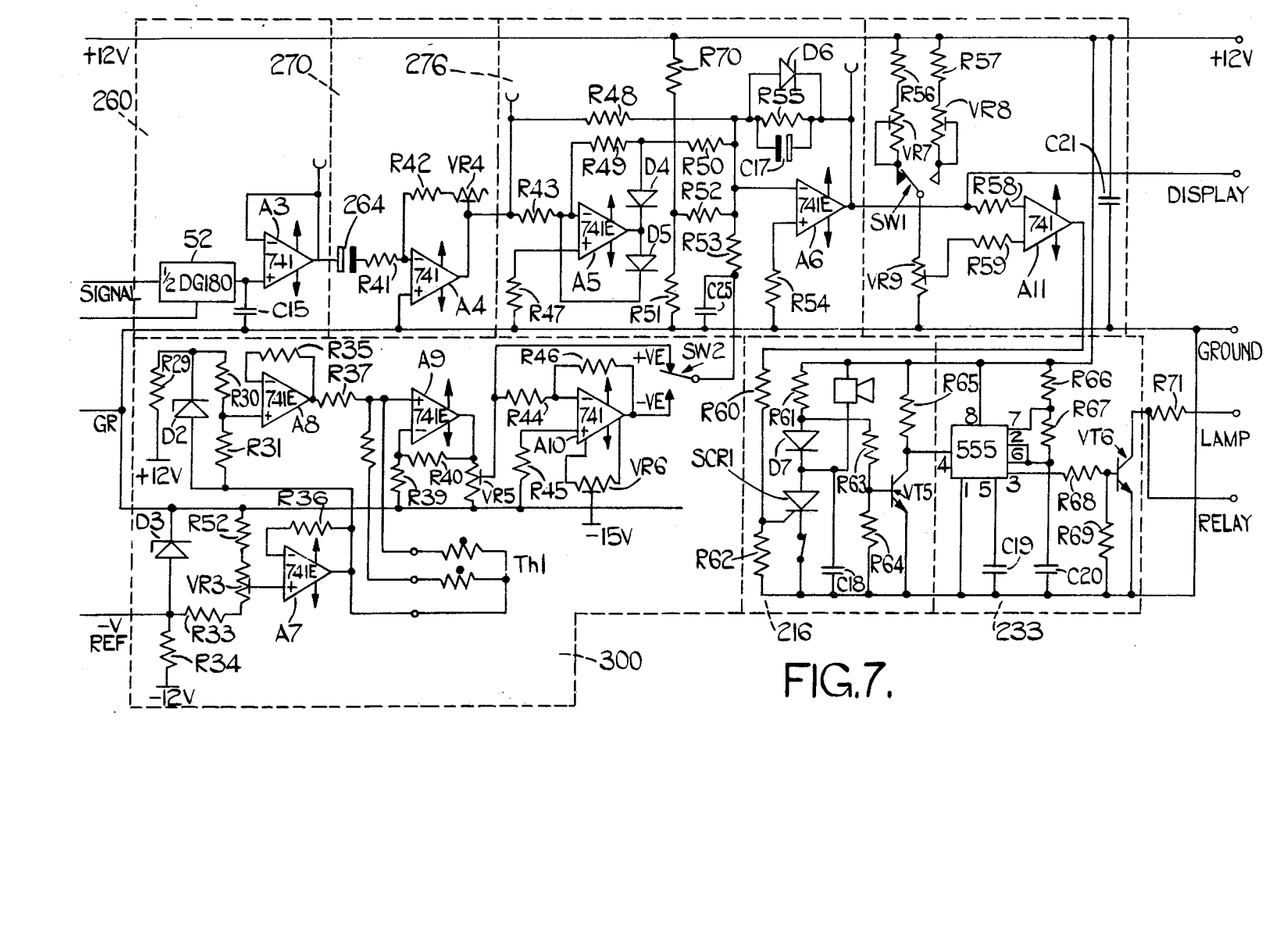

Turning now to the example of the invention shown in FIGS. 5 to 7, FIG. 5 shows the apparatus diagrammatically and bears some reference numerals corresponding to those shown in FIG. 1 but increased by 200. Thus a probe 210 and a reference capacitor 213 are connected to two terminals of the electronic switch device 211, but in this case there are resistors 210a and 213a in parallel with probe 210 and the reference capacitor 213 respectively. Also in parallel with the probe 210 is a variable conductance circuit 210b. The timing oscillator 230 which controls the electronic switch 211 is connected to the latter by a frequency dividing circuit 230a. The h.f. oscillator 214 controlled by the switch 211 is connected to the transformer 239 associated with the frequency to voltage converter 240 via a further frequency divider circuit 214a. The buffer 257 connects the output of the converter 240 to the sample and hold circuit 260 which is a.c. coupled by capacitor 264 to the amplifier stage 270. The full wave rectifier 276 receives an input from the amplifier stage 270 and also an input from a temperature compensation circuit 300.

Turning now to FIG. 6, it will be seen that the electronic switch circuit is an integrated circuit type DG 180 BA (manufactured by SILICONIX LIMITED) which consists of two independent analog switch channels in which the probe 210 and the reference capacitor 213 are connected respectively. The variable conductance circuit 210b (in parallel with the probe 210) includes a field effect transistor $VT_1$ with its source connected to the earth rail, and its drain connected by a resistor $R_{13}$ to the non-earthed side of the probe 210. The field effect transistor $VT_1$, operates as a variable impedance under the control of an operational amplifier $A_1$ connected as an active integrator. The output terminal of the amplifier $A_1$ is connected via a resistor $R_{11}$ to the gate of the field effect transistor $VT_1$. A resistor $R_{12}$ is connected between the gate and drain of the field effect transistor $VT_1$. The amplifier $A_1$ has its non-inverting input terminal connected to the earth rail and its inverting input terminal connected by a resistor $R_9$ to the output terminal of another operational amplifier $A_2$ connected as differential amplifier. Feedback around the amplifier $A_1$ is provided by a resistor $R_{10}$ and a capacitor $C_3$ in series between the output terminal and the inverting terminal of the amplifier $A_1$.

The amplifier $A_2$ is, as mentioned above connected as a differential amplifier and is arranged to compare the d.c. level on the resistor 210a with a fixed reference level. This fixed reference level is derived from a $-Vref$ rail and the components for deriving the $-Vref$ voltage are included in the temperature compensation circuit 300, to be described hereinafter. A potentiometer $VR_2$ is connected in series with "padding" resistors $R_2$ and $R_3$ between the $-Vref$ rail and the earth rail and its slider is connected by a resistor $R_4$ to the non-inverting input terminal of the amplifier $A_2$, a resistor $R_5$ connecting this same terminal to the earth rail. A resistor $R_1$ and a capacitor $C_1$ are connected in series between the non-earthed side of the probe 210 and the earth rail, a resistor $R_{72}$ connecting the junction of resistor $R_1$ and capacitor $C_1$ to the inverting input terminal of the amplifier $A_2$. A feedback resistor $R_6$ is connected between output terminal of the amplifier $A_2$ and its inverting input terminal. A resistor $R_{14}$ connects the junction of the resistor $R_{13}$ and 210a to the $-Vref$ rail.

The potentiometer $VR_2$ is initially set up so that the output of the amplifier $A_2$ is zero when the probe 210 is in position. In this condition the output of the amplifier $A_1$ held constant at a value such that the voltage across the resistor 210a is a fixed value. If there is a change in the conductivity of the material in the probe 210 (as distinct from its dielectric constant which is the parameter being measured), this voltage will drift and the output of the amplifier $A_2$ will go negative or positive accordance to the sign of the change in conductivity. This in turn will cause the output of the amplifier $A_1$ to fall or rise so that impedance of the field effect transistor falls or rises to compensate for the change in conductivity. Thus only changes in the capacitance of the probe 210 can influence oscillator 214 as the composition of the material in the probe changes, the overall conductivity being maintained constant.

The electronic switch device 211 serves as in FIGS. 1 to 4, to connect either the probe 210 or the reference capacitor 213 via a capacitor $C_{23}$ to the TRIGGER, DISCHARGE and THRESHOLD terminals of an integrated circuit timer $T_1$ (which may be one half of a dual timer circuit type 556 of well known type), which terminals are also connected to a $+5.6V$ supply rail by a common resistor $R_{15}$. The RESET terminal of the $T_1$ is connected to the $+5.6$ supply rail and its CONTROL VOLTAGE terminal is connected to the earth rail by a capacitor $C_{24}$, the non-earthed side of which is connected by one channel of a further DG 180 electric switch circuit $S_1$ to the slider of a potentiometer $VR_1$ connected in series with two padding resistors $R_{16}$ and $R_{17}$ between the $+5.6V$ rail and the earth rail. The control terminal of this channel of switch $S_1$ is connected to the same source (yet to be described) as that control terminal of the switch circuit 211 which is associated with the channel of switch 211 in which the probe 21o is connected.

The source of the control signals for the electronic switches 211 and $S_1$ is an integrated circuit edge-triggered flip flop circuit (one half of a Texas Instruments Integrated circuit type SN 74L74). The Q sand $\overline{Q}$ output terminals of this circuit are connected to the control terminals of the two channels of the switch 211. The CLEAR terminal is connected to the $+5.6$ volt rail and the D input terminal is connected to the $\overline{Q}$ output terminal. The CLOCK input terminal is connected to the OUTPUT terminal of a further timer circut $T_2$ (again ½ of a type 556. ic.). The CONTROL VOLTAGE terminal of the timer $T_2$ is connected by a capacitor $C_7$ to the ground rail and its RESET terminal and connected to the $+5.6V$ supply rail. The INPUT and DISCHARGE terminals of the timer $T_2$ are connected together and by a capacitor $C_6$ to the earth rail. The THRESHOLD terminal is connected by a resistor $R_{18}$ to the $+5.6V$ supply rail and by a resistor $R_{19}$ to the INPUT and DISCHARGE terminals. The timer produces output pulses of a given frequency and mark-space ratio. Since the flip-flop is edge-triggered it effectively halves the frequency and provides a stable 1:1 mark to space ratio for switching the switch circuit 211.

A similar ½ SN 74L74 integrated circuit edge-triggered flip flop circuit constitutes the divider 214a and the Q output terminal of this circuit is connected by a resistor $R_{20}$ and capacitor $C_8$ in series to one end of the primary winding of the transformer 239, the other end of which is connected to the +5.6V supply rail. This rail is connected to a +12V supply rail by a resistor $R_{21}$ and is regulated by a zener diode $D_1$ bridged by two capacitors, $C_4$ and $C_5$ in parallel.

The frequency to voltage converter 240 and the buffer 257 are the same as in FIGS. 1 to 4.

Turning now to FIG. 7 the output of the buffer 257 is applied to a further electronic switch $S_2$, which may be constituted by the other channel of the DG 180 integrated circuit used for switch $S_1$, and which constitutes the gating element of the sample and hole circuit 260. The control terminal of this switch $S_2$ is connected to the output terminal of the timer circuit $T_2$ and it controls connection of the buffer 257 to a signal storage capacitor $C_{15}$. An operational amplifier voltage follower $A_3$ provides the high impedance necessary to prevent loss of the charge on the capacitor $C_{15}$.

It will be noted that negative going edges of the pulsed signal from the timer $T_2$ effect operation of the divide by two circuit 230a whereas switch $S_2$ is "Closed" by a high signal at its control terminal. Thus switch $S_2$ is "opened" immediately before the switch 211 is operated and conducts therefore for a short time in each cycle immediately before the switching operation starts, and well after the spikes resulting from the last switching operation have disappeared.

The amplifier stage 270 employs an operational amplifier $A_4$ connected in inverting mode with an input resistor $R_{41}$ connected via the coupling capacitor 264 to the output terminal $A_3$, and a feedback path constituted by a resistor $R_{42}$ and a variable resistor $VR_4$ in series.

The output terminal of the amplifier $A_4$ is connected by a resistor $R_{43}$ to the inverting input terminal of an operational amplifier $A_5$ forming a first stage of the active full wave rectifier 276. The non-inverting input terminal of this amplifier $A_5$ is connected to the earth rail by a resistor $R_{47}$ and its output terminal is connected to the cathode of a diode $D_4$ and the anode of a diode $D_5$. The anode of the diode $D_4$ is connected by a resistor $R_{49}$ to the inverting input terminal of the amplifier $A_5$, the cathode of the diode $D_5$ being connected directly to this inverting input terminal. A further operational amplifier $A_6$ forms the second stage of the active full wave rectifier and has its non-inverting input terminal connected to the earth rail by a resistor $R_{54}$. Its inverting input terminal is connected by a resistor $R_{48}$ to the output terminal of the amplifier $A_4$, by a resistor $R_{50}$ to the anode of the diode $D_4$ by a resistor $R_{52}$ to the common point of two resistors $R_{70}$ and $R_{51}$ in series between the +12V rail and the earth rail and by a resistor $R_{53}$ to the output terminal of the temperature compensation circuit 300. The values terminal of the temperature compensation circuit 300. The values of the resistors $R_{43}$, $R_{48}$, $R_{49}$ and $R_{55}$ are chosen in known manner so that the magnitude of the gain of the rectifier circuit is the same for negative and positive inputs. Feedback around the amplifier $A_6$ is provided by the parallel combination of a resistor $R_{55}$, a capacitor $C_{17}$ and a diode $D_6$ with its anode connected to the non-inverting input terminal of the amplifier $A_6$ and its cathode connected to the output terminal thereof.

The temperature compensation circuit 300 includes a zener diode $D_2$ and a resistor $R_{34}$ connected in series between the earth rail and the −12V rail to provide the −Vref signal referred to above. The −Vref rail is connected by a resistor $R_{33}$ to one end of a potentiometer $VR_3$ the other end of which is connected by a resistor $R_{52}$ to the earth rail. The slider of the potentiometer $VR_3$ is connected to the non-inverting input terminal of an operational amplifier $A_7$ which has a feedback resistor $R_{36}$ connected between its inverting input and output terminals so as to act as a voltage follower.

The output terminal of the amplifier $A_7$ is connected to the anode of a zener diode $D_2$ the cathode of which is connected to a resistor $R_{29}$ to the +12V rail. A pair of resistors $R_{30}$, $R_{31}$ are connected in series across the zener diode $D_2$ and their common point is connected to the non-inverting input terminal of an operational amplifier $A_8$, again connected as a voltage follower with a feedback resistor $R_{35}$. The two amplifiers $A_7$ and $A_8$ establish stable voltage levels a fixed voltage apart at levels set by adjustment of the potentiometer $VR_3$.

A temperature sensing network is connected between the output terminals of the amplifiers $A_7$ and $A_8$ and consists of a fixed resistor $R_{37}$ and one part of a centre-tapped thermistor $Th_1$ in series between amplifier outputs, the other part of the thermistor $Th_1$ being connected in series with a resistor $R_{38}$ across said one part thereof. The junction of the resistor $R_{37}$ and said one part of the thermistor $Th_1$ is connected to the non-inverting input terminal of an operational amplifier $A_9$ which is connected as a fixed gain non-inverting amplifier with its gain determined by two resistors $R_{39}$ and $R_{40}$ in series between the output terminal of the amplifier $A_9$ and the earth rail with the junction of these resistors connected to the inverting input terminal. A potentiometer $VR_5$ is also connected between the output terminal of the amplifier $A_9$ and the earth rail and its variable point is connected by a resistor $R_{44}$ to the inverting input terminal of an operational amplifier $A_{10}$ connected as a unity gain inverting amplifier with a feedback resistor $R_{46}$ and a further resistor $R_{45}$ connecting the non-inverting input terminal to the earth rail. A potentiometer $VR_6$ is connected in conventional manner to the amplifier $A_{10}$ to enable the inherent input offset of the amplifier to be nulled.

The output terminal of the amplifier $A_{10}$ and the slider of the potentiometer $VR_5$ are connected to two terminals of a selector switch $SW_2$, the common terminal of which is connected by the resistor $R_{53}$ to the inverting input terminal of the amplifier $A_6$ as aforesaid.

The potentiometers $VR_3$ and $VR_5$ are adjusted to provide the required position and slope of the characteristic of the temperature compensation circuit, the switch $SW_2$ determining the polarity of the slope. These three adjustments enable the circuit 300 to be matched to substantially any oil composition to give the required temperature compensation for the composition, it being understood that the thermistor, $Th_1$ is immersed in the oil in use.

The output terminal of the amplifier $A_6$ is connected to the display 275 and is also connected by a resistor $R_{58}$ to the non-inverting input terminal of an operational amplifier $A_{11}$ operating as a voltage comparator. The non-inverting input terminal of amplifier $A_{11}$ is connected by a resistor $R_{59}$ to the slider of a potentiometer $VR_9$ one end of which is connected to the earth rail and the other end of which is connected to the common terminal of a switch $SW_1$ with its terminals connected via two variable resistors $VR_7$, $VR_8$ and two fixed resistors $R_{56}$, $R_{57}$ respectively to the +12V rail. The variable resistors $VR_7$ and $VR_8$ are adjusted to set up two different threshold values which are selected using the switch $SW_1$.

The output terminal of the amplifier $A_{11}$ is connected to the trigger circuit 216 which in the example shown in FIG. 7 includes an input voltage divider $R_{60}$, $R_{62}$ connecting the amplifier $A_{11}$ to the gate of a thyristor $SCR_1$. The cathode of the thyristor $SCR_1$ is connected to the earth rail through a normally closed switch (not shown) and the anode of the thyristor $SCR_1$ is connected to the terminal of the audible warning device and is also connected to the cathode of a diode $D_7$. The anode of which is connected by a resistor to the +12V rail. A capacitor $C_{18}$ connects the anode of the thyristor $SCR_1$ to the earth rail.

The anode of the diode $D_7$ is connected by two resistors $R_{63}$, $R_{64}$ in series to the earth rail and the junction of these is connected to the base of an npn transistor $VT_5$. The emitter of the transistor $VT_5$ is connected to the earth rail and its collected is connected by a resistor $R_{65}$ to the +12V rail and is also connected to the RESET terminal of an integrated circuit timer (type 555) $T_3$. The THRESHOLD and TRIGGER terminals of this timer $T_3$ are connected together and to the earth rail via a capacitor $C_{20}$. A resistor $R_{66}$ connects the +12V supply rail to the DISCHARGE terminal of the timer $T_3$ and a further resistor $R_{67}$ connects the DISCHARGE terminal to the THRESHOLD and TRIGGER terminals. The CONTROL VOLTAGE terminal of the timer $T_3$ is connected by a capacitor $C_{19}$ to the earth rail. The OUTPUT terminal of the timer $T_3$ is connected by two resistors $R_{68}$, $R_{69}$ in series to the earth rail with the junction of these resistors connected to the base of an npn transistor $VT_6$ which has its emitter connected to the earth rail. The collector of the transistor $VT_6$ is connected by a resistor $R_{71}$ to the warning lamp and directly to a relay winding (which may, if required, include a latching contact).

Normally, when the amplitude of the a.c. signal passed by coupling capacitor 264 is less than the value set by the variable resistors $VR_7$ and $VR_8$ and selected by the switch $SW_1$, the output of amplifier $A_{11}$ is negative. When the oil is contaminated sufficiently to increase the amplitude above this value, the output of the amplifier $A_{11}$ will go high, firing thyristor $SCR_1$ and thereby turning off transistor $VT_5$. The timer $T_3$ then operates as a low frequency oscillator (e.g. at 1Hz) so as to flash the lamp and intermittently energise the relay (which may be used to operate a remote warning or to control some function of a machine using the oil under test so as to shut down the machine or prevent certain operations of the machine which are undesirable when the oil is contaminated).

I claim:

1. Apparatus for the detection of water in oil comprising a capacitive probe unit through which the oil under test is caused to flow, a reference capacitor, switch means alternately connecting the capacitive probe and the reference capacitor into the circuit of an oscillator whereby the oscillator frequency is determined in alternate periods by the dielectric constant of the oil, a frequency to d.c. voltage converter connected to the output of the oscillator, filter means connected to the output of the converter for producing a signal fluctuating at the frequency of operation of said switch means and indicator means a.c. coupled to the output of the filter means sensitive to the amplitude of said fluctuating signal.

2. Apparatus as claimed in claim 1 in which said filter means includes a sample and hold circuit operated in synchronism with said switch means.

3. Apparatus as claimed in claim 2 including a switching oscillator for actuating said switch means, said switching oscillator being connected to the switch means through the intermediary of a frequency dividing circuit and said sample and hold circuit being connected to said switching oscillator so as to cause sampling to commence at an instant before switching of said switch means occurs.

4. Apparatus as claimed in claim 1 in which said indicator means includes a full wave rectifier and means sensitive to the output of the full wave rectifier.

5. Apparatus as claimed in claim 4 in which the full wave rectifier is an active full wave rectifier including an operational amplifier having a diode in its feedback circuit.

6. Apparatus as claimed in claim 4 including a voltage comparator connected to compare the output of the full wave rectifier with a reference voltage.

7. Apparatus as claimed in claim 6 including a trigger circuit operated by the comparator and arranged to activate warning means.

8. Apparatus as claimed in claim 7 in which said warning means comprises an audible warning device.

9. Apparatus as claimed in claim 7 in which said warning means includes a lamp and a low frequency oscillator for flashing said lamp.

10. Apparatus as claimed in claim 9 further including a relay connected to be energized by said low frequency oscillator.

11. Apparatus as claimed in claim 4 including a temperature compensation circuit including a temperature sensing element sensitive to the temperature of the oil under test and arranged to introduce a temperature dependent offset into the full wave rectifier.

12. Apparatus as claimed in claim 1 in which the first mentioned oscillator is connected to the frequency-to-voltage converter through the intermediary of a frequency divide-by-two circuit, whereby any fluctuations in the mark-to-space ratio of the first mentioned oscillator do not affect the output of the frequency-to-voltage converter.

13. Apparatus as claimed in claim 1 including a variable conductance circuit connected in parallel with the capacitive probe unit and means arranged to sense and maintain constant the combined conductance of the probe unit and the variable conductance circuit.

* * * * *